(12) United States Patent
Bierman

(10) Patent No.: US 7,316,679 B2
(45) Date of Patent: Jan. 8, 2008

(54) MEDICAL DEVICE CONNECTOR FITTING

(75) Inventor: Steven F. Bierman, Del Mar, CA (US)

(73) Assignee: Venetec International, Inc., San Diego, CA (US)

( * ) Notice: Subject to any disclaimer, the term of this patent is extended or adjusted under 35 U.S.C. 154(b) by 477 days.

(21) Appl. No.: 09/767,207

(22) Filed: Jan. 22, 2001

(65) Prior Publication Data

US 2002/0099360 A1   Jul. 25, 2002

(51) Int. Cl.
*A61M 25/18* (2006.01)

(52) U.S. Cl. .................. 604/535; 604/533; 604/534; 604/174; 128/DIG. 26

(58) Field of Classification Search ........ 604/533–538, 604/174–180; 128/DIG. 26
See application file for complete search history.

(56) References Cited

U.S. PATENT DOCUMENTS

| | | |
|---|---|---|
| 747,360 A | 12/1903 | Barry |
| 1,043,683 A | 11/1912 | Fieser |
| 1,104,955 A | 7/1914 | Bellows |
| 1,113,080 A | 10/1914 | Wilson |
| 2,446,599 A | 8/1948 | Knaggs |
| 2,525,398 A | 10/1950 | Collins |
| 2,533,961 A | 12/1950 | Rousseau et al. |
| 2,675,829 A | 4/1954 | Livers |
| 2,868,564 A | 1/1959 | Arras |
| 3,064,648 A | 11/1962 | Bujan |
| 3,167,072 A | 1/1965 | Stone et al. |
| 3,245,567 A | 4/1966 | Knight |
| 3,394,950 A | 7/1968 | Jensen |
| 3,394,954 A | 7/1968 | Sams |
| 3,529,597 A | 9/1970 | Fuzak |
| 3,540,451 A * | 11/1970 | Zeman ................. 604/27 |
| 3,677,250 A | 7/1972 | Thomas |
| 3,686,896 A | 8/1972 | Rutter |
| 3,724,882 A | 4/1973 | Dehar |
| 3,766,915 A | 10/1973 | Rychlik |

(Continued)

FOREIGN PATENT DOCUMENTS

DE      23 41 297      4/1975

(Continued)

*Primary Examiner*—Kevin C. Sirmons
*Assistant Examiner*—Laura C. Schell
(74) *Attorney, Agent, or Firm*—Knobbe Martens Olson & Bear LLP

(57) ABSTRACT

A releasable medical device connector comprises a connector fitting with a spin nut which connects to an adaptor. The connector fitting has at least one radially extending member with a variable radius cross section. The spin nut is disposed upon the connector fitting proximal of the radially extending member and is both axially slidable and rotatable upon the elongated body of the connector fitting. A screw thread within a proximal portion of the spin nut is used to secure the tapering portion of the connector fitting to an external thread disposed upon the adaptor. To release the connector, the spin nut is unscrewed from the adaptor and slid so that a distal receptacle of the spin nut engages the radially extending member of the connector fitting. With the spin nut and connector fitting engaged, the medical line can be released from the adaptor by twisting and pulling upon the spin nut. The radially extending member of the connector fitting may also be used to secure the medical line to a retainer comprising one or more slots.

32 Claims, 10 Drawing Sheets

U.S. PATENT DOCUMENTS

| | | | |
|---|---|---|---|
| 3,856,020 A | 12/1974 | Kovac |
| 3,900,026 A | 8/1975 | Wagner |
| 3,906,946 A | 9/1975 | Nordström |
| 3,918,679 A | 11/1975 | Silvana |
| 3,920,001 A | 11/1975 | Edwards |
| 3,942,228 A | 3/1976 | Buckman et al. |
| 3,973,565 A | 8/1976 | Steer |
| D243,477 S | 2/1977 | Cutruzzula et al. |
| 4,020,835 A | 5/1977 | Nordstrom et al. |
| 4,037,599 A | 7/1977 | Raulerson |
| 4,059,105 A | 11/1977 | Cutruzzula et al. |
| 4,068,870 A | 1/1978 | Whitney et al. |
| 4,082,094 A | 4/1978 | Dailey |
| 4,084,911 A | 4/1978 | DeWitt |
| 4,099,744 A | 7/1978 | Kutnyak et al. |
| 4,108,475 A | 8/1978 | Fleischer |
| 4,114,614 A | 9/1978 | Kesling |
| 4,114,618 A | 9/1978 | Vargas |
| 4,116,196 A | 9/1978 | Kaplan et al. |
| 4,123,091 A | 10/1978 | Cosentino et al. |
| 4,129,128 A | 12/1978 | McFarlane |
| 4,133,312 A | 1/1979 | Burd |
| 4,142,527 A | 3/1979 | Garcia |
| 4,150,673 A * | 4/1979 | Watt ............................ 604/408 |
| 4,161,177 A | 7/1979 | Fuchs |
| D256,162 S | 7/1980 | Haerr et al. |
| 4,224,937 A | 9/1980 | Gordon |
| 4,250,880 A | 2/1981 | Gordon |
| 4,316,461 A | 2/1982 | Marais et al. |
| 4,324,236 A | 4/1982 | Gordon et al. |
| 4,326,519 A | 4/1982 | D'Alo et al. |
| 4,362,156 A | 12/1982 | Feller, Jr. et al. |
| 4,392,853 A | 7/1983 | Muto |
| 4,397,647 A | 8/1983 | Gordon |
| 4,405,163 A | 9/1983 | Voges et al. |
| D273,993 S | 5/1984 | Schulte et al. |
| 4,449,975 A | 5/1984 | Perry |
| 4,453,933 A | 6/1984 | Speaker |
| 4,474,559 A | 10/1984 | Steiger |
| 4,480,639 A | 11/1984 | Peterson et al. |
| 4,516,968 A | 5/1985 | Marshall et al. |
| 4,585,435 A | 4/1986 | Vaillancourt |
| 4,633,863 A | 1/1987 | Filips et al. |
| 4,650,473 A | 3/1987 | Bartholomew et al. |
| 4,660,555 A | 4/1987 | Payton |
| 4,711,636 A | 12/1987 | Bierman |
| 4,742,824 A | 5/1988 | Payton et al. |
| 4,752,292 A | 6/1988 | Lopez et al. |
| 4,792,163 A | 12/1988 | Kulle |
| 4,795,429 A | 1/1989 | Feldstein |
| 4,826,486 A | 5/1989 | Palsrok et al. |
| 4,834,702 A | 5/1989 | Rocco |
| 4,834,716 A | 5/1989 | Ogle, II |
| 4,838,858 A | 6/1989 | Wortham et al. |
| D302,304 S | 7/1989 | Kulle et al. |
| 4,852,844 A | 8/1989 | Villaveces |
| 4,857,058 A | 8/1989 | Payton |
| 4,863,432 A | 9/1989 | Kvalo |
| 4,880,412 A | 11/1989 | Weiss |
| 4,897,082 A | 1/1990 | Erskine |
| 4,898,587 A | 2/1990 | Mera |
| 4,919,654 A | 4/1990 | Kalt |
| 4,934,375 A | 6/1990 | Cole et al. |
| 4,955,864 A | 9/1990 | Hajduch |
| 4,966,582 A | 10/1990 | Sit et al. |
| 4,976,700 A | 12/1990 | Tollini |
| 4,981,469 A | 1/1991 | Whitehouse el al. |
| 4,997,421 A | 3/1991 | Palsrok et al. |
| 5,037,397 A | 8/1991 | Kalt et al. |
| 5,047,021 A * | 9/1991 | Utterberg ................... 604/533 |
| D323,390 S | 1/1992 | Paine et al. |
| 5,084,026 A | 1/1992 | Shapiro |
| 5,113,571 A | 5/1992 | Manska |
| 5,135,506 A | 8/1992 | Gentelia et al. |
| 5,147,322 A | 9/1992 | Bowen et al. |
| 5,156,641 A | 10/1992 | White |
| 5,192,273 A | 3/1993 | Bierman et al. |
| 5,192,274 A | 3/1993 | Bierman |
| D347,060 S | 5/1994 | Bierman |
| 5,342,317 A | 8/1994 | Claywell |
| 5,344,406 A | 9/1994 | Spooner |
| 5,344,414 A | 9/1994 | Lopez et al. |
| 5,346,479 A | 9/1994 | Schneider |
| 5,352,211 A | 10/1994 | Merskelly |
| 5,354,282 A | 10/1994 | Bierman |
| 5,354,283 A | 10/1994 | Bark et al. |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,395,344 A | 3/1995 | Beisang, III et al. |
| 5,413,562 A | 5/1995 | Swauger |
| 5,449,349 A | 9/1995 | Sallee et al. |
| 5,456,671 A | 10/1995 | Bierman |
| 5,468,228 A | 11/1995 | Gebert |
| 5,470,321 A | 11/1995 | Forster et al. |
| 5,147,322 A | 1/1996 | Bowen et al. |
| 5,484,425 A | 1/1996 | Fischell et al. |
| 5,496,283 A | 3/1996 | Alexander |
| 5,520,656 A | 5/1996 | Byrd |
| 5,522,803 A | 6/1996 | Teissenn-Simony |
| 5,527,293 A | 6/1996 | Zamierowski |
| 5,536,258 A * | 7/1996 | Folden ...................... 604/265 |
| 5,578,013 A * | 11/1996 | Bierman .................... 604/180 |
| 5,586,790 A * | 12/1996 | Bynum ........................ 285/89 |
| 5,643,217 A | 7/1997 | Dobkin |
| 5,681,290 A | 10/1997 | Alexander |
| 5,827,230 A | 10/1998 | Bierman |
| 5,830,189 A | 11/1998 | Chang |
| 6,152,913 A | 11/2000 | Feith et al. |
| 6,210,417 B1 | 4/2001 | Baudino et al. |

FOREIGN PATENT DOCUMENTS

| | | |
|---|---|---|
| DE | 198 33 181 | 1/2000 |
| EP | 0 114 677 | 8/1984 |
| EP | 0 169 704 | 1/1986 |
| EP | 0 247 590 | 12/1987 |
| EP | 0 263 789 | 4/1988 |
| EP | 0 356 683 | 3/1990 |
| EP | 0 367 549 | 5/1990 |
| GB | 2 063 679 | 6/1981 |
| GB | 2 086 466 | 5/1982 |
| GB | 2 146 405 | 4/1985 |
| WO | WO 80/01458 | 7/1980 |
| WO | WO 90/05559 | 5/1990 |
| WO | WO 91/16939 | 11/1991 |
| WO | WO 92/03070 | 3/1992 |
| WO | WO 92/03923 | 3/1992 |
| WO | WO 92/19309 | 11/1992 |
| WO | WO 99/64103 | 12/1999 |

* cited by examiner

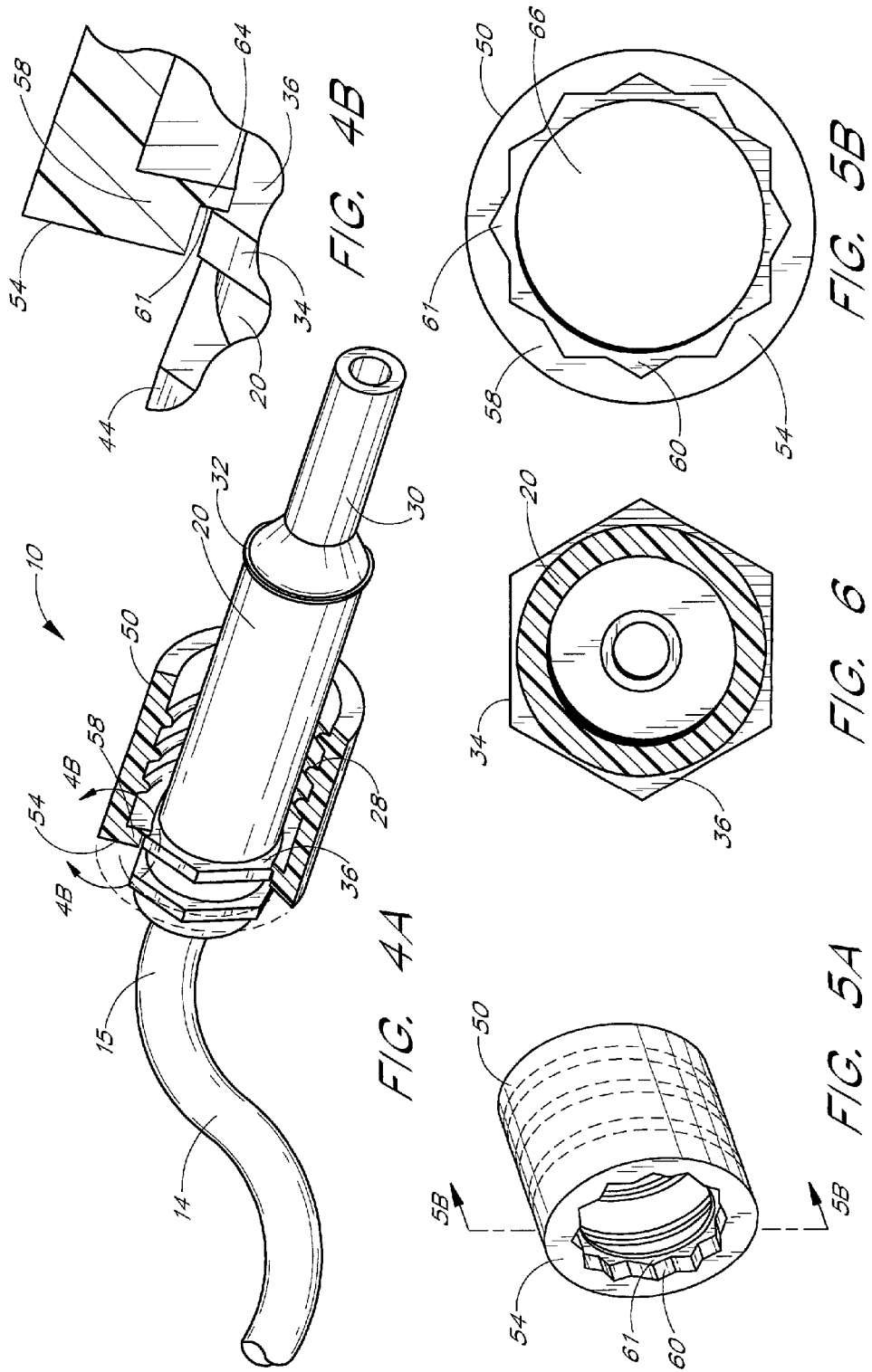

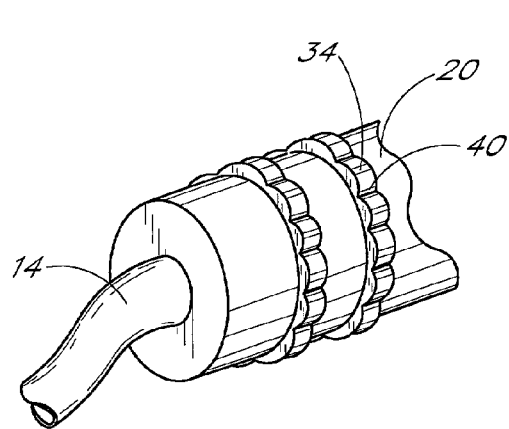 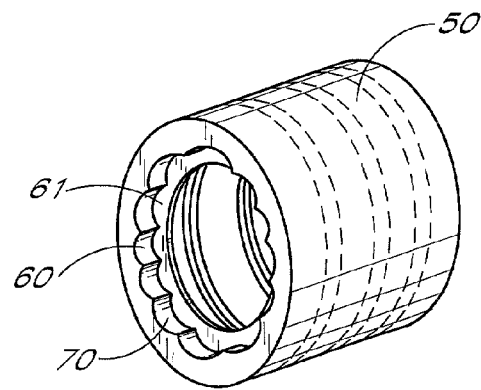
*FIG. 11A*  *FIG. 11B*
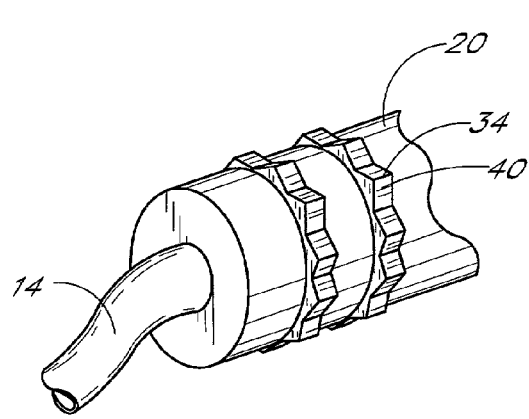 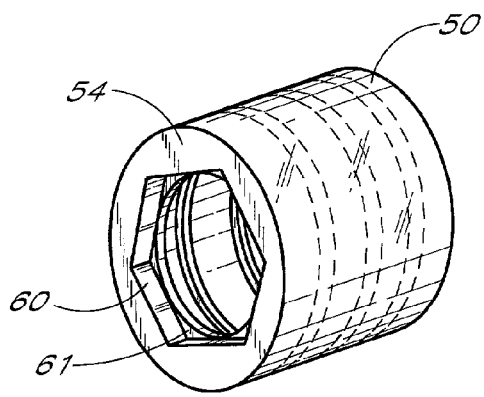
*FIG. 12A*  *FIG. 12B*

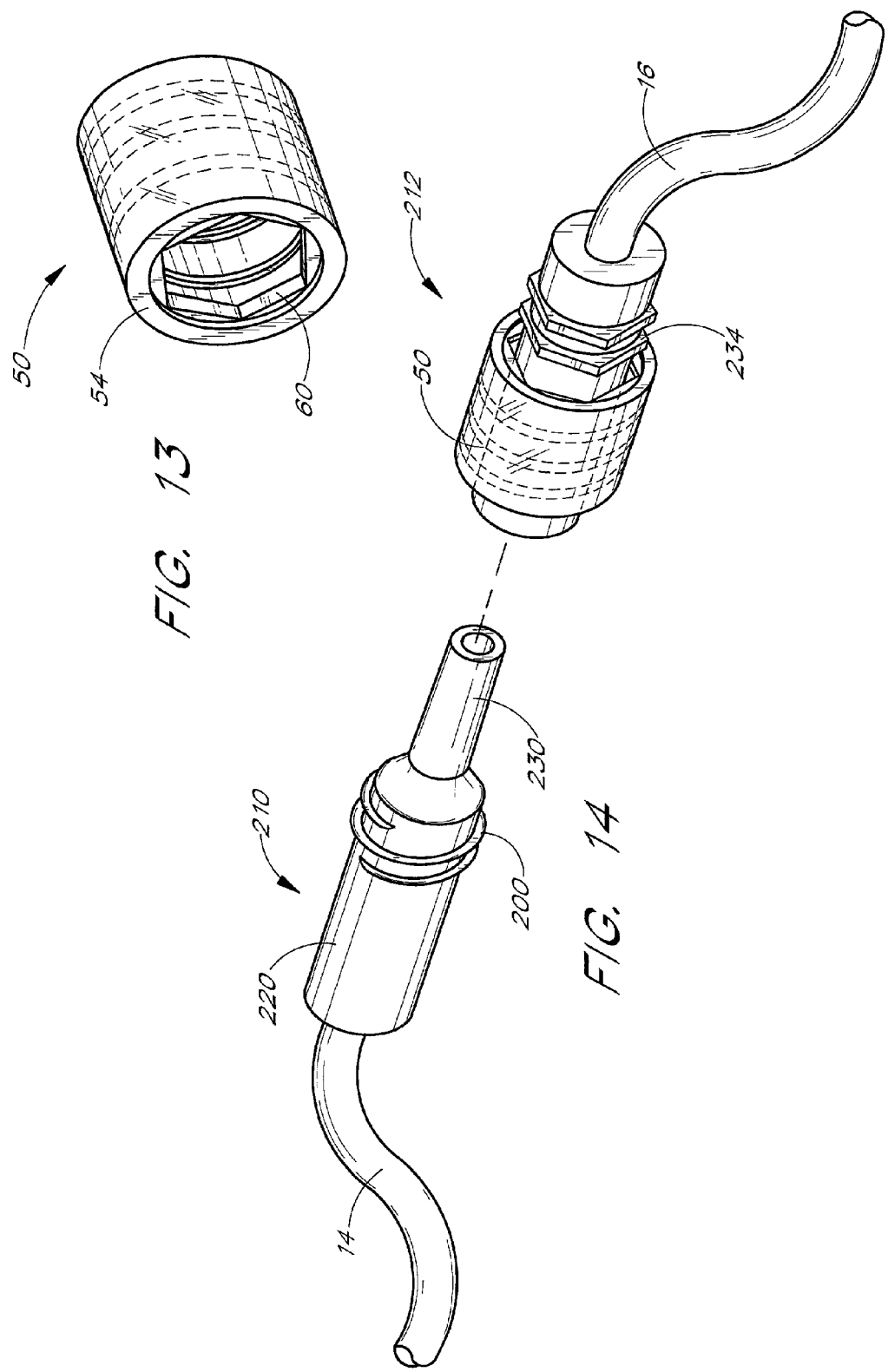

MEDICAL DEVICE CONNECTOR FITTING

BACKGROUND OF THE INVENTION

1. Field of the Invention

The present invention relates in general to a medical line connector fitting, and more specifically, to a releasable connector for use on an elongated medical article.

2. Description of Related Art

It is frequently desirable in the medical treatment of patients for medical personnel to have some form of access to the vasculature of the patient for delivery or withdrawal of fluids from the bloodstream. When such access is required over any period of time, it is common to introduce a catheter into the bloodstream of the patient to provide reusable access, for instance in order to deliver medication and/or fluids directly into the bloodstream of the patient. It may be desirable to leave such an intravenous catheter in place within the patient throughout treatment to avoid repeatedly having to introduce new catheters.

In intravenous applications, the catheter is generally short and includes a luer connector at one end that is designed for attachment to another medical line. Such a connector may also include a spin nut to lock the medical line to the catheter. In this way the same catheter may be connected to and released from different medical lines in order to exchange the medical lines without the need to introduce multiple intravenous catheters.

After use over an extended period of time, however, the luer connection between the medical line and the catheter hub may become stuck to each other and difficult to release. In particular, the force which was applied via the spin nut when locking the medical line to the catheter hub may press the medical line into the catheter with enough force that the medical line and catheter do not release upon unlocking the spin nut. In addition, fluid dries between the surfaces of the components of the luer connection, which further exacerbates the adhesion between the components.

In such circumstances, the medical technician may need to twist or pull the medical line apart from the catheter. The spin nut has a larger diameter and is easier to grasp than the medical line itself. Therefore a mechanism for transferring force from the spin nut to the medical line may be provided upon the luer connector in order to simplify release of the medical line from the catheter. One example of such a spin nut for use upon a luer connector is seen in U.S. Pat. No. 5,620,427 to Werschmidt et al.

The splines provided upon the Werschmidt device, however, allow only rotational force to be transferred between the spin nut and the medical line. The splines also do not impede axial motion of the spin nut in the proximal direction. As a result, the spin nut can migrate up onto the medical line, requiring medical personnel to locate the nut and thread it back into a proper position for usage when the medical line is to be attached or released.

Because of the importance and continued use of luer-type connectors between medical lines and intravenous catheters, there is a continued need for improvement in such releasable luer connectors.

SUMMARY OF THE INVENTION

One aspect of the present invention involves a connector fitting that is adapted to cooperate with a corresponding adaptor to couple together two medical components. For example, in one mode, the connector fitting can be adapted to connect to an adaptor on a distal side (i.e., away from the patient) of an indwelling intravenous catheter in order to couple an intravenous medical line to the adaptor. The connector fitting, however, can be disposed on either the upstream or downstream side of the resulting connection.

The connector fitting includes an elongated body. A rotatable spin nut is disposed upon the connector fitting body, and also is longitudinally slideable along the length of a portion of the connector fitting.

A radially extending member is disposed upon the connector fitting body. The spin nut includes a receptacle that is configured to engage the radially extending member when the spin nut is slid to its most distal position.

A possible feature of the connector fitting involves the radially extending member having a multi-sided (e.g., generally hexagonal) external cross section. The receptacle of the spin nut has a cooperating shape so as to receive and engage the radially extending member. The engagement between the spin nut and the radially extending member transfers rotational forces between these components when one of them is rotated.

Another possible feature of the connector fitting is that the receptacle of the spin nut has a shape which receives the radially extending member of the connector fitting and also has a wall that abuts axially against the radially extending member when the spin nut is engaged with the member. This allows for the transfer of axial force between the spin nut and the connector fitting when the two components are engaged.

In accordance with a more preferred mode, a connector fitting with a spin nut is used to connect a medical line to an adaptor. The connector fitting has an elongated body with a proximal tapering portion and a radially extending member disposed distally of the proximal tapering portion on the elongated body. The elongated body includes a lumen that communicates with ports on the proximal and distal sides of the connector fitting. The radially extending member has a variable radius cross-section. The spin nut is disposed upon the connector fitting proximal of the radially extending member and is both axially slideable and rotatable upon the elongated body of the connector fitting. The spin nut also includes a receptacle formed on its distal side. In order to apply force to the connector fitting, the spin nut is slid distally so that the receptacle of the spin nut engages the radially extending member of the connector fitting. With the spin nut and connector fitting engaged, the medical line may be moved (rotatably and/or axially) relative the adaptor by twisting and/or pulling upon the spin nut.

In accordance with another preferred mode, a connector fitting includes an elongated body which includes at least one radially extending member with at least one contact surface. A spin nut is also used which comprises a generally tubular body slidably and rotatably disposed upon the elongated body of the connector fitting. Desirably, the difference in radius between the external radius of the spin nut and the maximum radius of the radially extending member is less than the difference in radius between the maximum radius of the radially extending member and the external radius of the spin nut.

A preferred method of using this mode of the connector fitting to secure a medical line to the adaptor involves inserting the tapering portion of the connector fitting into the adaptor. The connector is then secured to the hub by sliding the spin nut to the proximal position and twisting it so that corresponding screw threads of the adaptor and the spin nut engage. To release the connector fitting from the adaptor, the spin nut is unscrewed from the adaptor and slid distally so that the receptacle of the spin nut engages the radially extending member. The spin nut is then twisted and pulled. This motion is transmitted to the body of the connector fitting by the engagement between the receptacle and the radially extending member to dislodge the tapering portion of the connector fitting from the adaptor.

Another aspect of the present invention involves a connector system for joining together two medical components (e.g., for joining a medical line and a catheter). The connector system comprises a connector fitting, as described above, and a medical line adaptor (e.g., a catheter hub). The connector fitting and the medical line adaptor are configured so as to engage to form a coupling between two medical components. In one mode, the connector fitting and the medical adaptor include interlocking threads to couple together these components; however, various aspects of the present invention can be practiced apart from such a luer-type connection.

The connector system can be used with an anchoring system. This combination provides a secure connection between the medical components and provides a secure anchor of the connection to the patient. The anchoring system includes a retainer which receives a least a portion of the connector fitting. The retainer has at least one receptacle (e.g., slot) that is adapted to receive the radially extending member on the connector fitting to inhibit longitudinal (i.e., axial) movement of the fitting relative to the retainer. In a preferred mode, the retainer includes a plurality of receptacles disposed longitudinally to offer multiple positions in which to position the connector fitting within the retainer. This affords the ability to coarsely align the connector fitting relative to the retainer before inserting the connector fitting into the retainer. The anchoring system also can include an anchor pad, which adheres to the patient's skin and on which the retainer is mounted.

Another aspect of the present invention involves the combination of the above-described connector fitting together with a retainer. The radially extending member of the connector fitting is configured to cooperate with a slot or other receptacle of the retainer when the radial member is not engaged with the spin nut. Such a retainer may include one or more slots so dimensioned to cooperate with the radially extending member of the connector fitting to hold the connector fitting in position relative to the retainer. The retainer also may be part of an anchoring system that further includes a base pad on which the retainer is mounted.

For purposes of summarizing the invention and the advantages achieved over the prior art, certain objects and advantages of the invention have been described above. Of course, it is to be understood that not necessarily all such objects or advantages be achieved in accordance with any particular embodiment of the invention. Those skilled in the art will recognize that the invention may be embodied or carried out in a manner that achieves or optimizes one advantage or group of advantages as taught herein without necessarily achieving other objects or advantages as may be taught or suggested herein. Thus, the connector fitting, and its combinations with an anchoring system and/or with a medical adaptor, can take various forms, and not all embodiments need include all of the aspects and features noted above. In addition, further aspects, features and advantages of this invention will become apparent from the detailed description of the preferred embodiments which follow.

BRIEF DESCRIPTION OF THE DRAWINGS

The above mentioned and other features of the invention will now be described with reference to the drawings of preferred embodiments of the present connector fitting and connector system. The illustrated embodiments are intended to illustrate, but not to limit the invention. The drawings contain the following figures:

FIG. 4A is a similar view to that shown in FIG. 3 and illustrates the spin nut engaged with a radially extending member of the connector fitting.

FIG. 4B is an enlarged view of the region within circle 4B-4B of FIG. 4A and illustrates the radially extending member abutting a wall of the spin nut receptacle.

FIG. 5A is a perspective view of a distal end of the spin nut showing the receptacle.

FIG. 5B is an enlarged distal end view of the spin nut illustrating the receptacle.

FIG. 6 is a cross-sectional view of the connector fitting taken along line 6-6 of FIG. 3 and illustrates a preferred form of the radially extending member.

FIG. 11A is a perspective view of a distal end portion of a connector fitting having a radially extending member configured in accordance with an additional preferred form, and FIG. 11B is a perspective view of the distal end of a spin nut with a correspondingly shaped receptacle to receive the radially extending member.

FIG. 12A is a perspective view of a distal end portion of a connector fitting having a radially extending member configured in accordance with an additional preferred form, and FIG. 12B is a perspective view of the distal end of a spin nut with a correspondingly shaped receptacle to receive the radially extending member.

FIG. 13 is a perspective view of a spin nut in yet another form which may be used with a connection system as shown in FIG. 14, below.

FIG. 14 is a perspective view of a connector system configured in accordance with another preferred embodiment of the present invention.

DETAILED DESCRIPTION OF PREFERRED EMBODIMENTS

The following description and examples illustrate in detail a preferred embodiment of the present connector system disclosed in the context of use with an exemplary medical line and intravenous catheter. The principles of the present invention, however, are not limited to intravenous catheters. It will be understood by those of skill in the art in view of the present disclosure that the releasable connector system described may be applied to other types of medical articles, including without limitation, catheters and fluid delivery or drainage tubes. One skilled in the art may also find additional applications for the devices and systems disclosed herein. Thus the illustration and description of the connector system in connection with the medical line and catheter are merely exemplary of one possible application of the connector system.

To assist in the description of these components of the connector system (see FIG. 1), the following coordinate terms are used. A "longitudinal axis" is generally parallel to the axis of the connector fitting 10. A "lateral axis" is normal to the longitudinal axis and is generally parallel to the plane of the skin of a patient upon which such medical lines are attached. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis.

The term "axial" as used herein refers to the axis of the medical line, and therefore is substantially synonymous with the term "longitudinal" as used herein. Also, the terms "proximal" and "distal", which are used to describe the present anchoring system, are used consistently with the description of the exemplary applications. Thus, proximal and distal are used in reference to the center of the patient's body. Therefore, the proximal end of any apparatus is the portion which is closer to the center of the patient's body, while the distal end of any structure is that which is located farther from the center of the patient's body.

The terms "upper," "lower," "top," "bottom," and the like, which also are used to describe the present anchoring system, are used in reference to the illustrated orientation of the embodiment. A detailed description of a preferred embodiment of the anchoring system, and its associated method of use, now follows.

Overview

Figure 1:
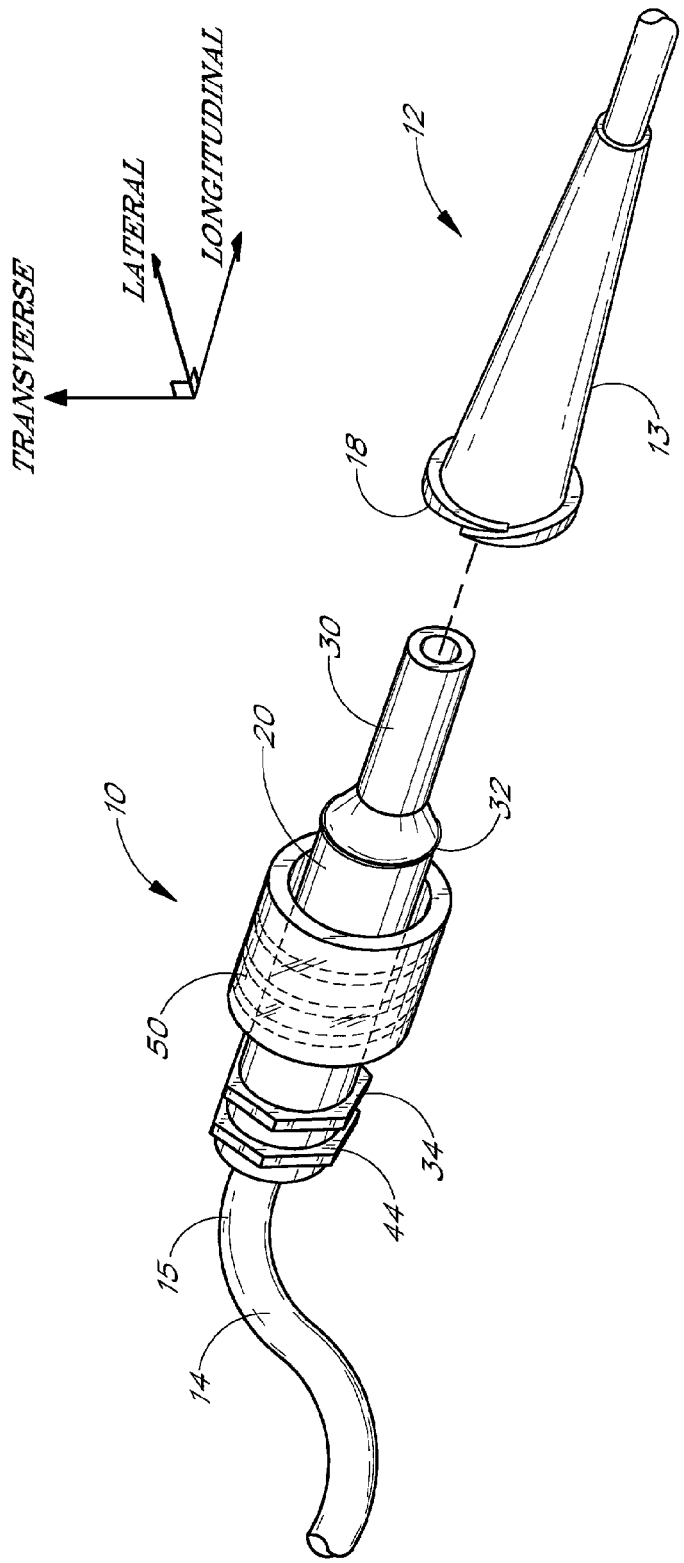
FIG. 1 is a perspective view of a connector system including a connector fitting configured in accordance with a preferred embodiment of the present invention with the connector fitting and an adaptor of the connector system disconnected.

As shown in FIG. 1, the illustrated and described embodiment of the medical line connector system comprises a connector fitting 10 and an adaptor 12, for example an adaptor for an intravenous catheter as illustrated in FIG. 1. The connector fitting 10 is preferably disposed upon the proximal end 15 of an exemplifying medical line 14. The medical line 14 may be connected to such devices as are useful in introducing or removing fluid from the patient, for example a drip bag, a dialysis machine, a blood monitor or any other device as is known to those of skill in the art.

In regard to the illustrated use of the connector fitting and the connector system to connect an intravenous line to an intravenous catheter, the catheter adaptor 12 is disposed at the distal end of a short percutaneous needle which is inserted proximally into the patient (not shown). The adaptor 12 and needle may desirably be left in position upon the patient during treatment while different medical lines 14 are connected to the adaptor 12 via the connector system. This advantageously allows a medical practitioner to avoid introduction of multiple catheters and multiple needle sticks into the patient for each different medical line which is to be connected. The adaptor 12 desirably includes an elongated tubular tapered region 13 with a central lumen which is in fluid connection with the lumen of the needle.

The adaptor 12 also may advantageously include an external screw thread 18 disposed upon the outer surface of the tubular portion 13 of the adaptor 12. The screw thread 18 may be used in association with a spin nut (described below) of the connector fitting 10 in order to securely interconnect the medical line 14 and the adaptor 12. In addition to a screw thread, other means may be used to connect the adaptor 12 to the connector fitting (as described below). These may include without limitation, pin and groove arrangements, latch and keeper arrangements, and such other systems as are known to those of skill in the art.

The connector fitting 10 comprises an elongated body 20 which is attached distally to the proximal end 15 of the medical line 14. The connector fitting 10 also comprises a proximal portion 30 which is desirably tapered along at least part of its longitudinal length so as to allow the most proximal region to fit within the tubular tapered portion 13 of the adaptor 12. The tapered proximal portion 30 of the connector fitting 10 also preferably includes a centrally disposed lumen which communicates with the lumen of the medical line 14.

When the proximal portion 30 of the connector fitting 10 is inserted into the tubular portion 13 of the adaptor 12, the lumen of the connector fitting is disposed in fluid communication with the lumen of the adaptor. This provides fluid communication between the medical line 14 and the patient, as understood from FIG. 2.

As shown in FIG. 1, the connector fitting 10 also has at least one radially extending member 34 disposed upon a distal region of the elongated body 20 of the fitting 10. Note that as shown in FIG. 1, it may be advantageous for the radially extending member to extend completely around the circumference of the connector fitting 10. A radially extending member which extends completely around the circumference of the fitting 10 allows the fitting 10 to be more easily inserted onto a retainer (as will be described below) with only a coarse alignment necessary between the fitting and retainer. Additionally, a member 34 which extends over the entire circumference allows the fitting and retainer to be interfaced without concern for any rotation the fitting may have around its own axis, because the member extends from the fitting at every circumferential position. A second radially extending member 44 may also be disposed distally upon the elongated body 20, as may additional radial members (not shown). The second radially extending member 44 can have a similar shape to the first radially extending member 34 or can have other shapes as well (e.g. circular).

A spin nut 50 is disposed upon the connector fitting 10 around the elongated body 20 of the fitting 10. The spin nut 50 is substantially cylindrical in form and is able to move upon the connector fitting 10. The spin nut 50 is capable of both rotational motion around the axis of the connector fitting 10 and axial motion in both the proximal and distal directions along the length of the elongated body 20 of the fitting 10. The range of axial motion of the spin nut is limited by the radially extending member 34 in the distal direction and by a retaining ridge 32 in the proximal direction. The spin nut also includes internal screw threads which are illustrated with phantom lines in FIG. 1.

Figure 2:
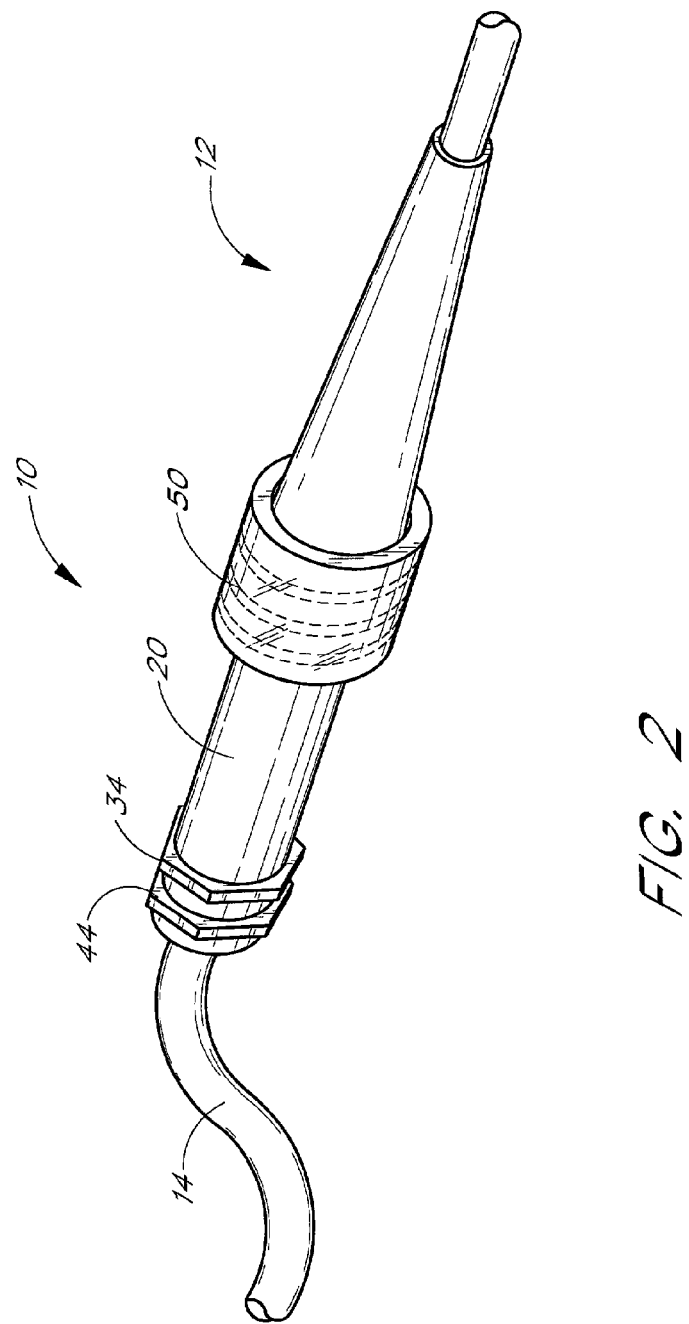
FIG. 2 is a perspective view of the connector system of FIG. 1 with the connector fitting and adaptor connected to each other.

As shown in FIG. 2, when the proximal portion 30 of the connector fitting 10 is inserted into the tubular portion 13 of the adaptor 12, the spin nut 50 may be moved in the proximal direction and twisted so as to engage the screw thread 18 of the adaptor 12 and lock the connector fitting 10 to the adaptor 12.

Connector Fitting and Spin Nut

Figure 3:
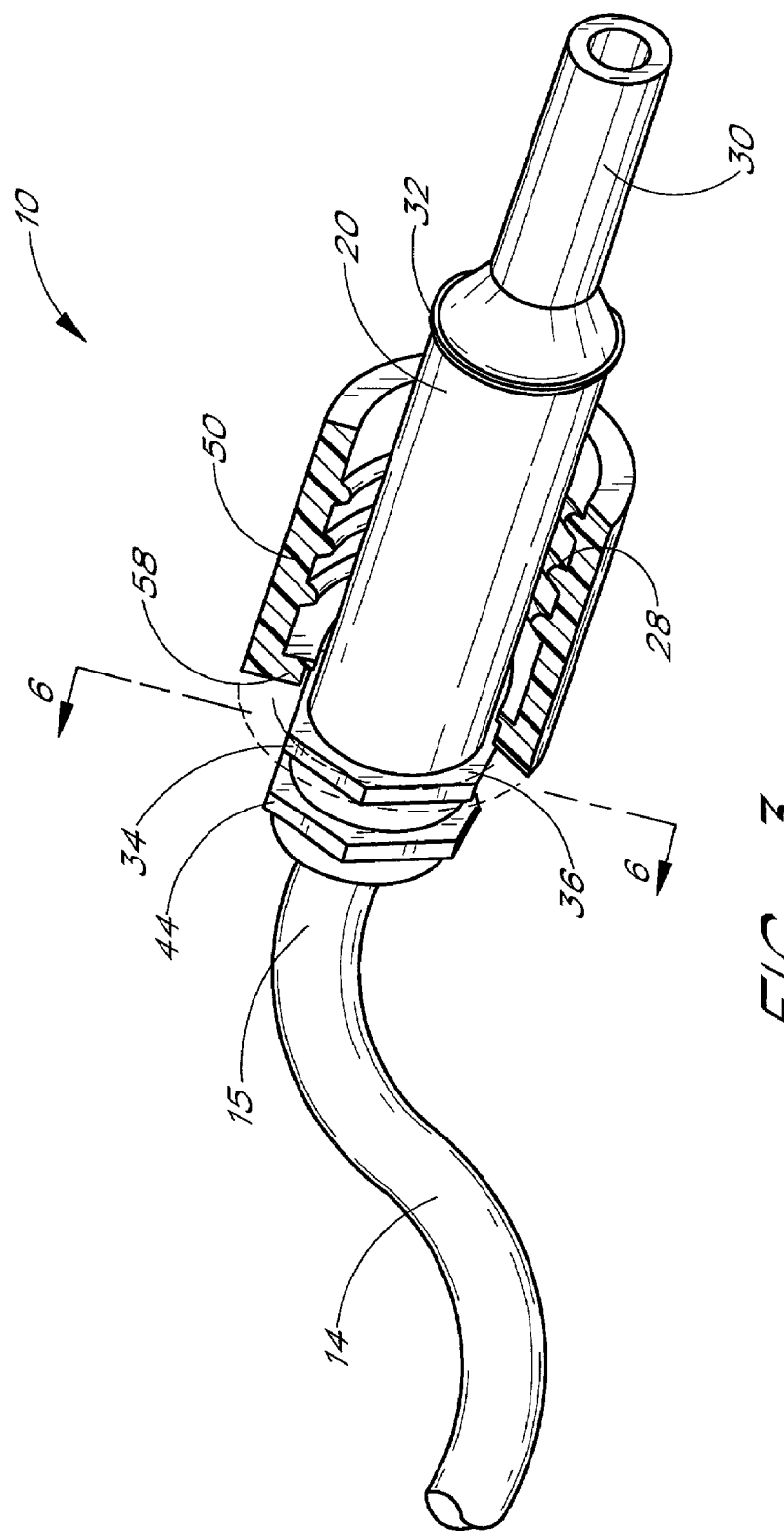
FIG. 3 is a perspective view of the connector fitting of FIG. 1 with a spin nut of the fitting shown partially in section.

FIG. 3 shows the connector fitting 10 with a cut-away view of the spin nut 50 in position upon the elongated body 20 of the fitting 10. The spin nut 50 is desirably disposed such that the central axis of the spin nut 50 is generally the same as the central axis of the elongated body 20 of the connector fitting 10. The spin nut 50 is free to rotate about and slide along the axis of the connector fitting 10.

The spin nut 50 desirably has an internal screw thread 28 disposed upon the inner surface of the spin nut 50. This screw thread 28 will engage with the screw thread 18 of the adaptor 12 when the adaptor 12 is secured to the connector fitting 10. The distal wall 58 of the spin nut 50 is also visible in the sectioned portion of FIG. 3. This wall 58 forms a distal end of the spin nut 50.

As noted above, the spin nut 50 is shown in FIG. 3 in a position which is neither fully distal nor fully proximal along the length of the elongated body 20 of the connector fitting 10. FIG. 4A shows the spin nut 50 and connector fitting 10 with the spin nut 50 in a fully distal position. When the spin nut 50 is in the distal position, the wall 58 of the spin nut 50 is positioned such that the distal surface 61 of the receptacle 60 of the spin nut 50 is resting against the proximal wall 36 of the radially extending member 34. This can be seen more clearly in FIG. 4B, which is an enlarged view of the portion of FIG. 4A labeled 4B-4B. In this position, the receptacle 60 receives at least a portion of the radially extending member 34.

With reference to FIG. 4B, it can be seen that the wall 58 of the spin nut 50 extends inwardly toward the axis of the spin nut 50 and ends in a lip 64 which extends inwardly from the wall 58. The inner surface of the lip 64 forms the opening 66 (see FIG. 5B) in the middle of the spin nut 50 through which the elongated body 20 of the medical line fitting 10 passes. The opening 66 preferably is slightly larger than the diameter of the elongated body 20.

Because the lip 64 is narrower in the axial direction than the wall 58, as can be seen in FIG. 4B, the distal surface 61 of the lip 64 and the distal surface of the wall 54 are at different longitudinal positions along the axial length of the spin nut 50. Because the distal surface 54 of the wall 58 is more distally located than the distal surface 61 of the lip 64, a recess is formed which comprises the receptacle 60 of the spin nut 50. When the spin nut 50 is in the fully distal position, as shown in FIGS. 4A and 4B, the radially extending member 34 is inserted into the receptacle 60. Preferably, when the spin nut 50 is in the distal position, the receptacle 60 of the spin nut will accept about at least one-third of the axial length of the radially extending member 34, and more preferably, about two-thirds of the axial length of the radially extending member 34.

As shown in FIGS. 5A and 5B, the receptacle 60 has a cross-sectional shape which forms a twelve-pointed star. As seen in FIG. 6, the radially extending member 34 has a cross-sectional shape which is substantially hexagonal. Other cross-sectional shapes may be used for both the receptacle 60 and the radially extending member 34, but desirably, the cross-sectional shape of the radially extending member 34 may fit within the cross-sectional shape of the receptacle 60. More desirably, the cross-sectional shape of the radially extending member 34 and the receptacle 60 are such that when the member 34 is within the receptacle 60 the largest radius of the member 34 is greater than the smallest radius of the receptacle.

By having a maximum radius of the member 34 being greater than the minimum radius of the receptacle 60, the walls of the receptacle will exert a torque upon the member 34 if the spin nut 50 is rotated while in the distal position. In this way, a twisting motion applied to the spin nut when in the distal position will be transferred to the connector fitting 10, allowing the spin nut 50 to be gripped when attempting to remove the connector fitting 10 from the adaptor 12.

Figure 7B:
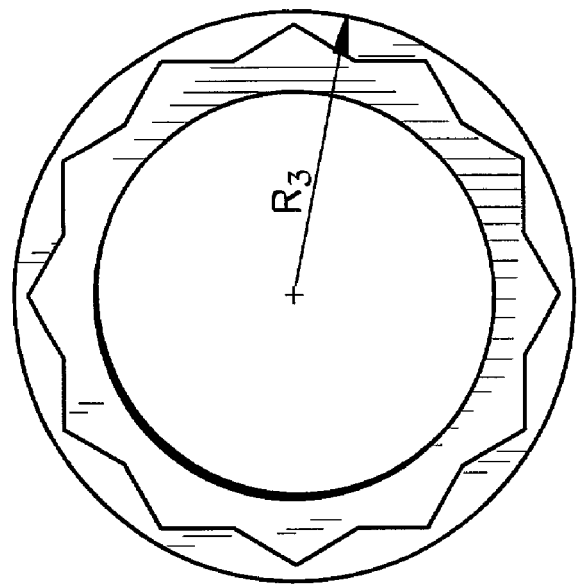
FIG. 7B is an enlarged distal end view of a spin nut illustrating another preferred form of the spin nut and receptacle.
Figure 7A:
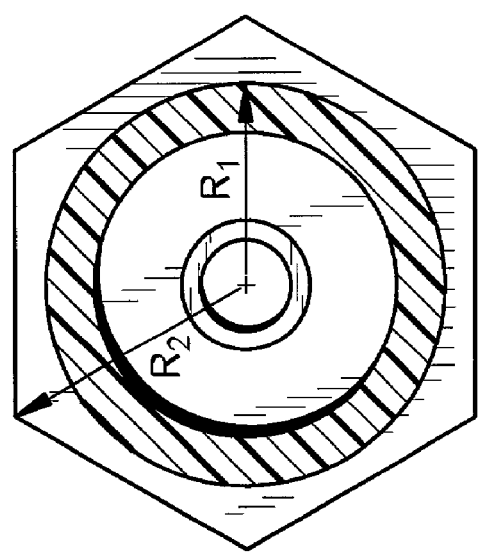
FIG. 7A is a cross-sectional view of an additional preferred form of the connector fitting.

With reference to FIGS. 7A and 7B, note that it may also be desirable to have the maximum radius $R_2$ of the radially extending member 34 (see FIG. 7A) be closer in size to the external radius of the spin nut (indicated as $R_3$ on FIG. 7B) than radius $R_2$ is to the radius of the elongated body 20 (indicated as $R_1$ on FIG. 7A) of the fitting 10. This increases the radial extent of the radially extending member 34 away from the surface of the elongated body 20 and provides for a better surface for the receptacle of the spin nut 50 to grip.

As shown in FIG. 5B, using a receptacle 60 with a twelve-pointed star shape and a member 34 with a hexagonal shape (as shown in FIG. 6), there are 12 different positions in which the receptacle 60 may be moved over the member 34 producing a snug fit. However, those of skill in the art will recognize that it is only necessary that a single position be available in which the receptacle 60 fits over the member 34, and it is not necessary that such a fit be snug. As pointed out above, as long as the member 34 fits within the cross section of the receptacle and the maximum radius of the member 34 is greater than the minimum radius of the receptacle 60, it will be possible to transfer torque from the spin nut 50 to the connector fitting 10 when the nut 50 is in the fully distal position.

In addition to providing a mechanism for the transfer of torque between the spin nut 50 and the connector fitting 10, the receptacle 60 also is capable of exerting a distally directed axial force upon the member 34. When the spin nut 50 is in the distal position, as shown in FIGS. 4A and 4B, the distal surface 61 of the lip which forms the face of the receptacle 60 is pressed against the proximal wall 36 of the radially extending member 34. Because of this contact, any force applied in the distal direction when the spin nut 50 is already in the distal position will be transferred, via the contact between these surfaces, to the member 34 and to the connector fitting body 20.

This interaction between the distal surface 61 of the lip 64 and the radially extending member 34 also inhibits migration of the spin nut 50 distally off of the end of the connector fitting 10 and onto the medical line 14. This maintains the spin nut 50 upon the connector fitting 10, eliminating the need for medical personnel to locate a spin nut which may have moved off of the fitting 10. This allows for more rapid and reliable release of the connector fitting 10 from the catheter adaptor 12.

Variations

As pointed out above, it is possible to use various shapes for the receptacle 60 and radially extending member 34 in order to allow the spin nut 50 to transfer force to the connector fitting 10. Several variations of spin nuts 50 and member designs are illustrated in FIGS. 8A to 12B. Throughout these figures, the spin nut 50 and elongated body 20 of the connector fitting 10 are consistently labeled for clarity. Except as noted below, the designs shown in FIGS. 8A to 12B may be substantially similar in construction and usage as the embodiment described above with reference to FIGS. 1 to 6. For instance, all of the designs include a distal wall 61 of the lip 64 which presses axially against the radially extending member 34 in order to transfer axial force between the spin nut 50 and the radially extending member 34.

Figure 8A:
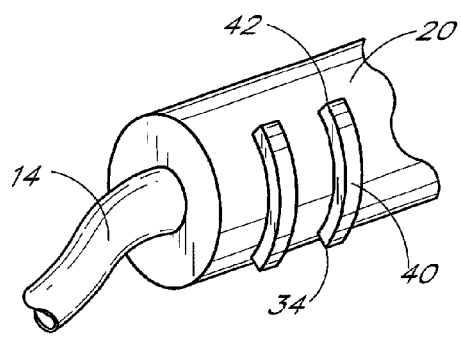
FIG. 8A is a perspective view of a distal end portion of a connector fitting having radially extending members configured in accordance with another preferred form.
Figure 9A:
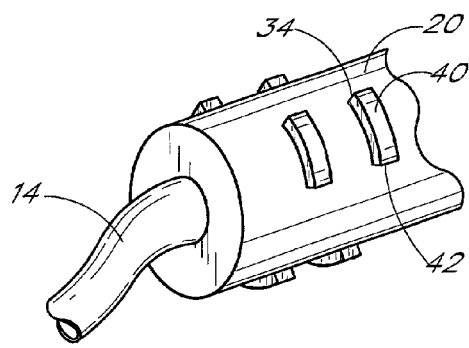
FIG. 9A is a perspective view of a distal end portion of a connector fitting having radially extending members configured in accordance with an additional preferred form.
Figure 10A:
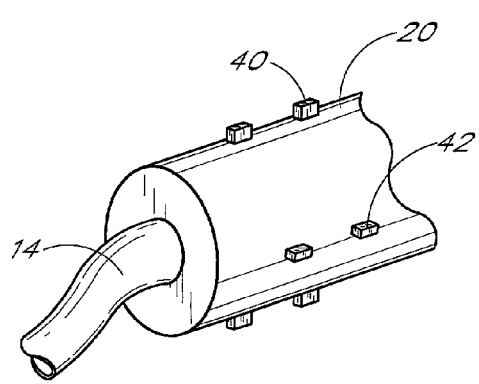
FIG. 10A is a perspective view of a distal end portion of a connector fitting having a radially extending member configured in accordance with another preferred form.

One type of variation for the radial member is shown in FIGS. 8A, 9A and 10A. Rather than a continuous hexagonal member, as shown in FIG. 4A, the radial member takes the form of projections 40 which extend radially from the elongated body 20 of the connector fitting 10. These projections 40 do not surround the entire circumference of the elongated body 20, but are desirably spaced approximately evenly about the circumference with spaces in between them.

FIG. 8A shows the distal end of a connector fitting 10 which uses a pair of projections 40 for each radially extending member. As can be seen, multiple sets of projections 40 may be included at different axial positions along the length of the elongated body 20. This corresponds to the use of multiple radially extending members illustrated in the embodiment shown in FIG. 4A.

Figure 8B:
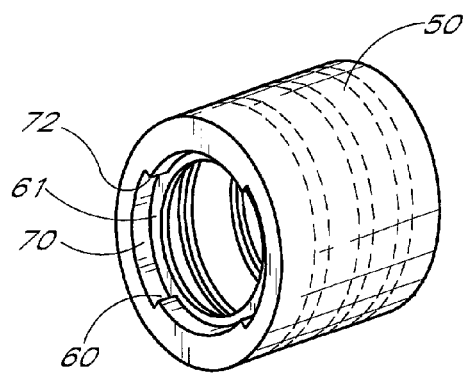
FIG. 8B is a perspective view of the distal end of a spin nut with correspondingly shaped receptacles to receive the radially extending members.

A spin nut 50 configured to operate in association with the connector fitting 10 of FIG. 8A is shown in FIG. 8B. This spin nut 50 is constructed substantially similarly to that described above, except for the cross sectional shape of the receptacle 60. The receptacle 60 is desirably configured so that its cross section provides a shape into which the projections 40 of the radially extending member 34 of the connector fitting 10 can be inserted. As seen in FIG. 8B, this shape may take the form of an inner, circular region and sockets 70 spaced about the circumference of the receptacle 60. The sockets 70 preferably have a radius larger than that of the inner region, and also larger than the radius of the projections 40 of the fitting 10.

The sockets 70 are desirably each larger than the projections 40 of the fitting 10. The sockets 70 and projections 40 are also desirably similarly spaced about the circumference of the spin nut 50 and fitting 10. This allows the spin nut 50 of FIG. 8B to be moved distally along the elongated body 20 of the connector fitting 10 of FIG. 8A and the projections 40 to fit within the sockets 70 of the spin nut 50. Because of the two-fold rotational symmetry of the arrangement, there are two positions in which the receptacle 60 will accept the projections 40.

In this distal position, the spin nut 50 is capable of exerting distal force upon the projections 40, just as the spin nut in the earlier embodiment exerted distal force against the radially extending member 34. In addition, because the radius of the projection 40 and the elongated body 20 is different, a radial wall 42 is created at the end of each projection. A similar radial wall 72 is created on the spin nut 50 at the end of each socket 70.

When the spin nut 50 is in a distal position, any rotation of the spin nut 50 will eventually bring the radial wall 72 of the spin nut 50 into contact with the radial wall 42 at the end of one or more of the projections 40. This allows torque to be transferred from the spin nut 50 to the fitting 10 in order to facilitate removal of the connector fitting 10 from the adaptor 12.

Note that it is not necessary that the fit between the projections 40 and the sockets 70 be particularly snug. For instance, in FIG. 8A, projections 40 are shown which extend through an arc of about 90°. Similarly, in FIG. 8B, sockets 70 are shown which extend through an arc of about 90°. However, if the projections 40 on the elongated body 20 were only to extend through an arc of about 75°, the receptacle 60 would still accept the projections 40, and the same spin nut 50 would still be able to exert the same distal force and torque upon the connector fitting 10.

As long as the projections 40 of the radially extending member 34 are able to fit inside the receptacle 60 of the spin nut 50 and the largest radius of the projections 40 is greater than the smallest radius of the receptacle 60, the spin nut 50 will cooperate with the fitting 10 to transfer the desired distal force and torque. However, when the projections 40 are significantly smaller than the sockets 70, there will be a certain amount of play in the fit between the radially extending member 34 and the receptacle 60. This means that if the spin nut 50 is rotated, it may rotate through an arc before a radial wall 72 of the socket 70 comes into contact with a radial wall 42 of a projection 40.

Figure 9B:
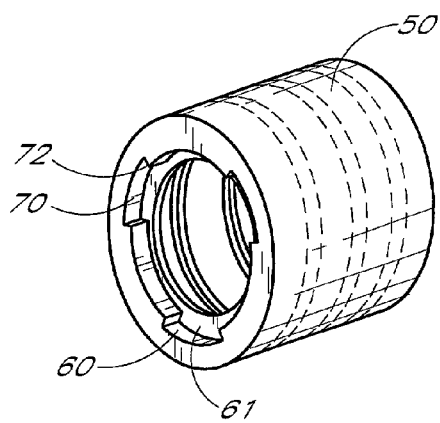
FIG. 9B is a perspective view of the distal end of a spin nut with correspondingly shaped receptacles to receive the radially extending members.

FIGS. 9A and 9B show a connector fitting 10 and spin nut 50 designed and operating substantially similarly to those shown in FIGS. 8A and 8B, except that there are three projections 40 for each radial member 34, and there are three corresponding sockets 70 upon the receptacle 60. Such an arrangement functions in substantially the same manner as that described above. In the illustrated arrangement, the sockets 70 and projections 40 each extend through an arc of about 60°. Note that it is desirable that the sockets 70 extend through a slightly greater arc than the projections 40 in order to allow the projections 40 to more easily fit within the sockets 70 when the spin nut 50 is in the distal position.

Figure 10B:
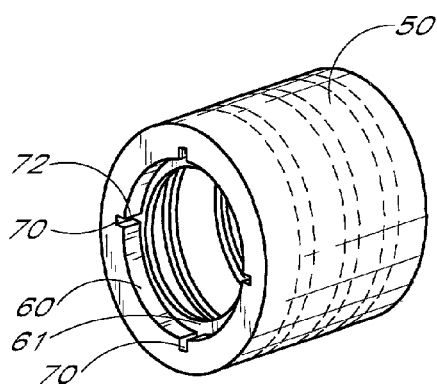
FIG. 10B is a perspective view of the distal end of a spin nut with correspondingly shaped receptacles to receive the radially extending member.

FIGS. 10A and 10B show a connector fitting 10 and spin nut 50 designed and operating substantially similarly to those shown in FIGS. 8A to 9B, except that there are four projections 40 for each radial member 34, and there are four corresponding sockets 70 upon the receptacle 60. Unlike the previous embodiments, the projections 40 and sockets 70 of elongated body 20 and spin nut 50 are not evenly sized with the gap between them. The projections 40 and sockets 70 extend through an arc of only about 10°.

Note that it is also possible in some combinations to make use of spin nut 50 with a fitting 10 having a different number of projections 40 than the spin nut 50 has sockets 70. For instance, the connector fitting 10 of FIG. 10A having four projections 40 each extending through 10° and spaced about 90°0 from one another could be used with a spin nut 50 as in FIG. 8B, which has only two sockets 70 spaced apart 180°, as long as each socket extends through an arc of more than about 100°.

In this way, the fit between the socket 70 and the projections 40 is still fairly snug; however, there are now four positions in which the radial member 34 may fit within the receptacle 60, as opposed to the two positions which the spin nut 50 may accept the projections of the fitting 10 of FIG. 8A.

Another configuration of the radially extending member 34 and receptacle 60 is shown in FIGS. 11A and 11B. Here, the radial member 34 comprises a series of twelve curved protrusions 40 which extend around the entire circumference of the elongated body 20. The receptacle 60 of the spin nut 50 has a set of sockets 70 of shape to snugly accept and engage the protrusions 40. Those of skill in the art will recognize that the precise profile of the protrusions 40 need not be as shown in the figure, nor need there be twelve protrusions. However, it may be desirable in some circumstances that the number of protrusions 40 match the number of sockets 70 in order to allow the radial member 34 to fit within the receptacle 60.

Unlike the designs shown in FIGS. 8A to 10B, the protrusions 40 and sockets 70 have a curving profile in this embodiment. As a result, there are no radial walls on either the receptacle 60 or the radial member 34. However, because the profile of both the protrusions 40 and sockets 70 vary in radius along their length, contact is made between the receptacle 60 and the radial member 34 which allows for rotational torque to be transferred from the spin nut 50 to the adaptor elongated body 20.

FIG. 12A shows a connector fitting 10 which has a radial member 34 with protrusions 40 having substantially the same profile as the receptacle 60 of the spin nut 50 in FIGS. 5A and 5B. Such a fitting 10 may be used as a variation to the fitting 10 shown in FIG. 4A with the spin nut 50 of FIGS. 5A and 5B. FIG. 12B shows a spin nut 50 with a hexagonal receptacle 60 of substantially the same profile as the radial member 34 of the fitting 10 of FIG. 4A. This spin nut 50 may be used with the adaptor of FIG. 4A as a variation to the spin nut 50 of FIGS. 5A and 5B.

Catheter Adaptor and Spin Nut

Another arrangement for a medical line connector system is shown in FIGS. 13 and 14. The spin nut 50 used in such a system is shown in FIG. 13 and is substantially the same as the spin nut 50 shown in FIG. 12B. However, the spin nut 50 is used differently, as is shown in FIG. 14.

FIG. 14 shows a medical line adaptor 210 connected to the proximal end of a medical line 14. The medical line adaptor 210 includes an elongated body 220 and a proximal portion 230. The elongated body 220 is attached to a medical line 14. An external screw thread 200 is disposed upon the outer surface of the elongated body 220. This adaptor 210 provides the same male portion of the connector system that is provided in the connector fitting 10 of FIG. 1.

Another connector fitting 212 is shown at the distal end of a second medical line 16. This fitting 212 provides the female portion of the connector system that is provided by the adaptor 12 of FIG. 1. The spin nut 50 is disposed along the outside of the tubular section of the connector fitting 212, rather than along the elongated body 220 of the medical line adaptor 210. In addition, the radially extending member 234 is disposed upon the connector fitting 212 as well.

In essence, the embodiment shown in FIG. 14 places the spin nut 50 and radial member 234 upon the female member 212 of the connector system, rather than upon the male member, as shown in previous figures. The operation of the system is substantially the same in such an embodiment, however, the spin nut 50 is now used to transfer translational and rotational forces to the female member 212 of the connector system.

The features disclosed with respect to the radial member 34 in use upon the connector fitting 10 shown in FIG. 1 and 2 may also be applied to the use of the radial member 234 on the connector fitting 212 as well. This includes the various cross sectional shapes of the receptacles 60 and radial member 34, such as those disclosed in FIGS. 8A to 12B, and such other features as are known by those of skill in the art.

Operation

In operation, as seen in FIGS. 1 and 2, a connector system in accordance with an embodiment of the present invention may be used to secure a connector fitting 10 to an adaptor 12, as well as to facilitate removal of the connector fitting 10 from the adaptor 12 when needed. The operation of the system will be described with reference to the embodiment of the device shown in FIGS. 1 and 2. However, those of skill in the art will recognize that the same operation may desirably be applied to any of the variations described herein.

In connecting the medical line 14 to the adaptor 12, the medical technician first inserts the proximal end 30 of the connector fitting 10 into the tubular portion 13 of the adaptor 12. The spin nut 50 is then pushed in the proximal direction until the screw threads 28 of the spin nut 50 contact the screw threads 18 of the adaptor 12. The spin nut 50 may then be twisted to secure the connection between the connector fitting 10 and the adaptor 12. This produces the configuration shown in FIG. 2.

In order to remove the connector fitting 10 from the adaptor 12, the spin nut 50 is twisted until the screw threads 28 of the spin nut 50 are disengaged from the screw threads 18 of the adaptor 12. The spin nut 50 is then slid distally along the length of the elongated body 20 of the connector fitting 10 until the receptacle 60 on the distal portion of the spin nut 50 is pressed against the radially extending member 34 of the connector fitting 10.

The spin nut 50 is then rotated while maintaining distal pressure upon it (relative to the connector fitting 10), until the radially extending member 34 slides into the receptacle 60 of the spin nut 50. The medical technician may then twist and pull upon the spin nut 50, and the force of twisting and pulling will be transferred to the connector fitting 10. By doing this while holding the adaptor 12 in place, the connector fitting 10 may be removed from the adaptor 12 without having to grip the connector fitting 10 directly.

Connector Fitting and Anchoring System

Figure 15:
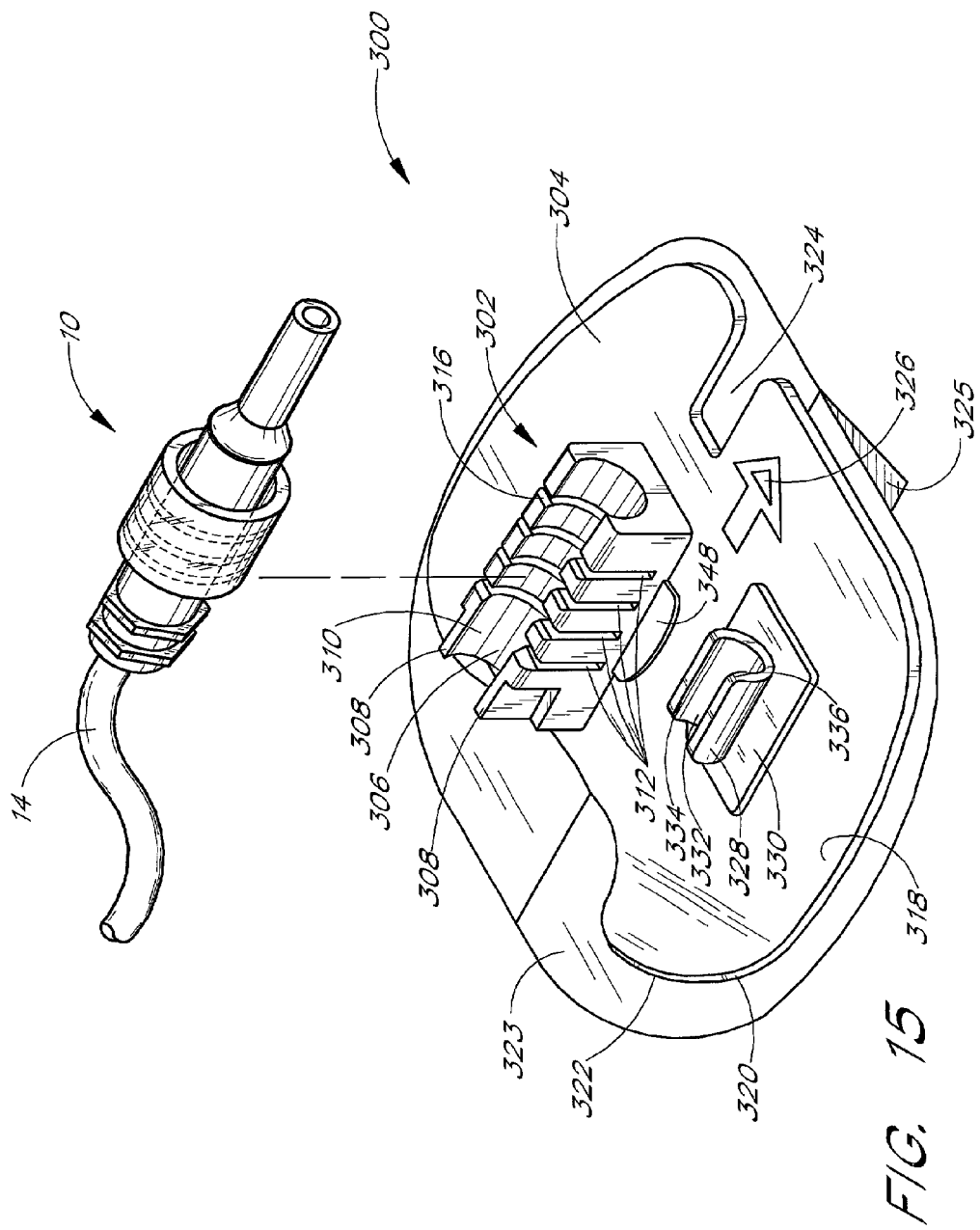
FIG. 15 is a perspective view of the connector fitting of the system shown in FIG. 1 with an exemplary anchoring system.
Figure 16:
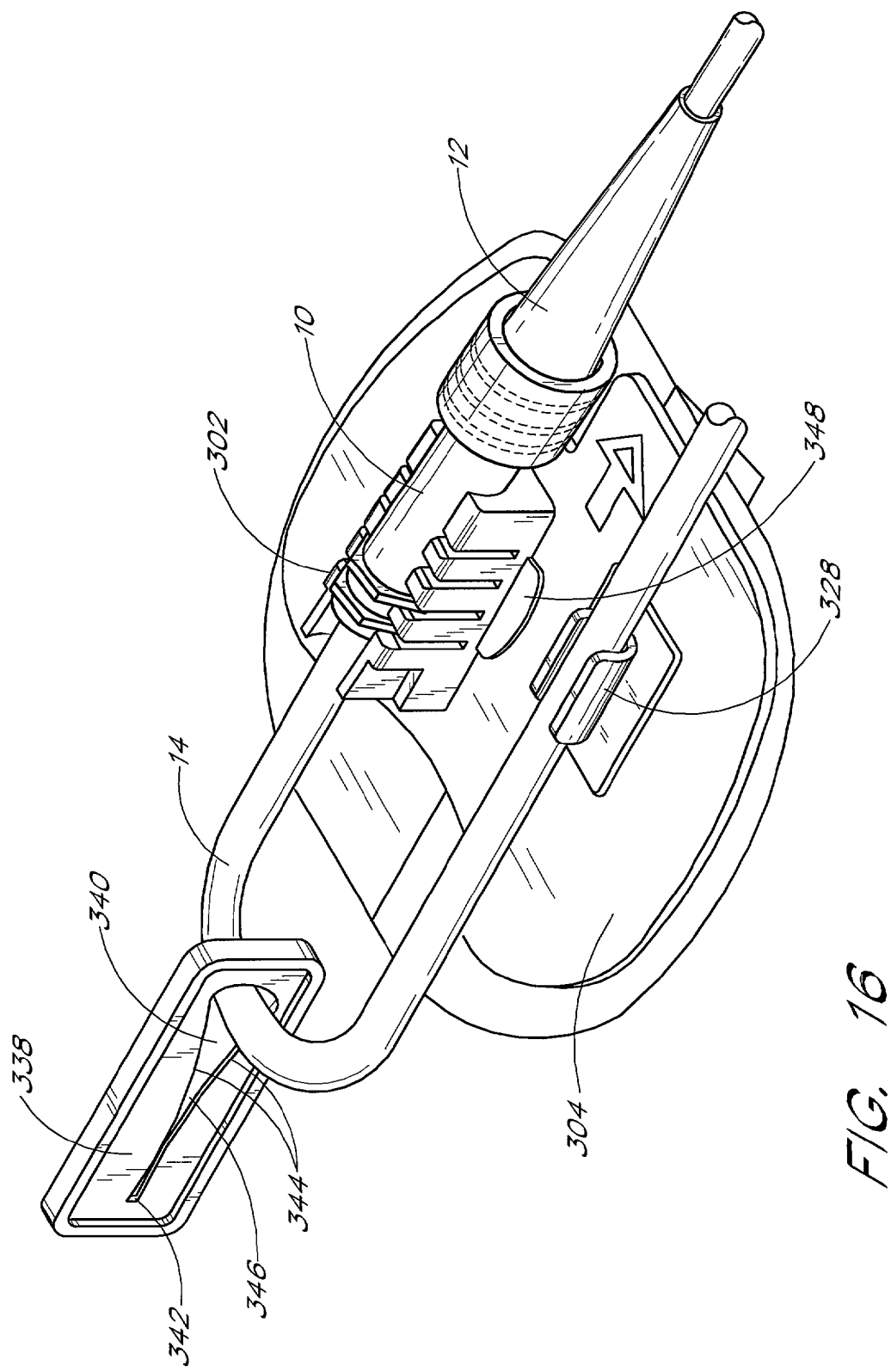
FIG. 16 is a perspective view of the connector system of FIG. 1 in use with an exemplary medical line anchoring system from FIG. 15.

FIGS. 15 and 16 illustrate an anchoring system 300 for use with a connector system 10 as is disclosed above. The connector system 10 may be snapped into position upon a retainer 302 of the anchoring system 300. The retainer 302 is configured to secure the connector fitting 10. The retainer 203 is disposed upon a base pad 304 which may desirably be used to anchor the retainer to the skin of a patient.

Retainer

The retainer 302 has a generally parallelepiped shape defining a central channel 306 interposed between a pair of opposing longitudinal walls 308. The central channel 306 extends through the retainer 302 along an axis which is generally parallel to the longitudinal axis of the retainer 302.

The central channel 306 has a generally circular cross-sectional shape which is truncated at an upper end to form a generally U-shaped channel having an upper opening 310. The central channel 306 has a diameter sized to receive the radial member 34 of the connector fitting 10. In a preferred embodiment, the diameter of the central channel 306 generally matches that of the radial member 34 or is slightly larger.

In cross-section, the central channel 306 extends through an arc greater than 180° about the channel axis such that the transverse length of the opening 310 is less than the diameter of the central channel 306. In an exemplary embodiment, the central channel 306 extends through an arc of about 200° about the channel axis.

The channel axis is desirably angled relative to the surface of the pad 304. An incident angle formed between the surface of the pad 304 and the channel axis is desirably less than 45°. The angle desirably ranges between 0° and 30°. In an exemplary embodiment for intravenous use, the angle preferably equals approximately 7°. In another exemplary embodiment for arterial use, the angle preferably equals about 22°. In a further exemplary embodiment, for peripherally inserted central catheters (PICC), the angle preferably equals 0°.

Each wall 308 of the retainer 302 comprises a uniform set of slots 312. While only a single slot 312 need be used, the use of two or more slots 312 requires only coarse alignment between the retainer 302 and the fitting 10 when pressing the radial member or members of the fitting into the slots 312. More preferably, the set of slots comprises less than seven slots 312. In an exemplary embodiment, as illustrated in FIGS. 15 and 16, the set comprises four slots 312.

Each slot 312 is sized to accept a radial member 34 of the fitting 10 to prevent longitudinal displacement of the connector fitting 10, as discussed in detail below. Each slot 312 desirably has a rectangular shape. The slots 312 extend through both walls 308 of the retainer 302 and open into the central channel 306. The width of each slot 312 (measured longitudinally) is desirably slightly greater than the width of a radial member 34 of the connector fitting 10, measured in the longitudinal direction in order to allow the slot 312 to receive a radial member 34, as discussed below.

Each slot 312 has a height as measured in the transverse direction between an upper edge of the longitudinal wall 308 and the bottom of the central channel 306. The height of the slot 312 desirably equals approximately the width of the radial member 34 such that the radial member 34 does not protrude from the retainer 302 in the transverse direction.

Alternatively, the slots 312 can be replaced by protrusions (not shown) which extend from the longitudinal wall 308 into the central channel 306. If a plurality of protrusions is used, the radial member 34 is placed between adjacent protrusions. As will be understood by one of skill in the art, the central channel 306 width may need to be increased to accommodate the width of the radial member 34 if protrusions are used instead of slots 312

The upper edge of the longitudinal wall 308 comprises a series of chamfers 316, each of which slopes into a slot 312. That is, the portion of upper edge of the longitudinal wall 308 which surrounds a slot 312 includes a pair of chamfers 316, with one chamfer 316 located on either side of the slot 312. The chamfers 316 slope downward toward the slot 312 to facilitate the insertion of the radial member 34 of the connector fitting 10 into the slot 312.

The retainer 302 is made of relatively stiff plastic material (e.g., polycarbonate), but is somewhat flexible such that the connector fitting 10 forces the upper edges of the longitudinal walls 308 transversely outward when a medical practitioner presses the connector fitting 10 into the central channel 306 of the retainer 302. When the fitting 10 sits in the central channel 306, the upper edges of the walls 308 snap transversely inward to their original position to securely hold the fitting 10 within the retainer 302.

An adhesive desirably attaches the retainer 302 to a base pad 304. Alternatively, the retainer 302 may be attached to the base pad 304 by non-adhesive means (e.g., embedding or otherwise weaving the retainer 302 into the base pad 304).

Base Pad

Still referring to FIGS. 15 and 16, the flexible base pad 304 comprises a laminate structure with an upper foam layer 318 (e.g., closed-cell polyethylene foam), and a lower adhesive layer 320. The lower adhesive layer 320 also forms the lower surface 322 of the base pad 304. The lower surface 322 desirably is a medical-grade adhesive and can be either diaphoretic or nondiaphoretic, depending upon the particular application. Such foam with an adhesive layer is available commercially from Avery Dennison of Painsville, Ohio. Although not illustrated, it will be understood that the base pad 304 can include suture holes in addition to the adhesive layer 320 to further secure the base pad 302 to the patient's skin.

In an alternative embodiment, a hydrocolloid adhesive may advantageously be used upon the base pad 304 for attaching the pad to the skin of the patient. The hydrocolloid adhesive has less of a tendency to excoriate the skin of a patient when removed. This may be particularly important for patients whose skin is more sensitive or fragile, such as those with a collagen deficiency.

A surface of the upper foam layer 318 constitutes an upper surface of the base pad 304. The upper surface can be roughened by corona-treating the foam layer 318 with a low electric charge. The roughened or porous upper surface can improve the quality of the adhesion between the base pad 304 and the retainer 302 and tub clip 328. In the alternative, the flexible base pad 304 can comprise a medical-grade adhesive lower layer, an inner foam layer and an upper paper or other woven or non-woven cloth layer.

A removable paper or plastic backing 323 desirably covers the bottom adhesive layer 322 before use. The backing 323 preferably resists tearing and is divided into a plurality of pieces to ease attachment of the pad 304 to the patient's skin. Desirably, the backing is split along the center line of the flexible base pad 304 in order to expose only half of the adhesive bottom surface 322 at one time. The backing 323 also advantageously extends beyond at least one edge of the base pad 304 to ease removal of the backing from the adhesive layer 322.

One or more tabs 325 may be attached to a portion of the backing 323 which extends beyond the flexible base pad 304. In an exemplary embodiment, the tabs 325 have the same laminate structure as the flexible base pad 304. The tabs 325 also can be formed by the paper backing 323 extending beyond the edge of the base pad 304. The tabs 325 may also include indicia in the form of dots, words, figures or the like to indicate the placement of fingers when removing the backing 323 from the base pad 304.

The tabs 325 of course can be designed in a variety of configurations. For example, the tab need not be located along a center line of the base pad; rather, the tab can be located along any line of the base pad in order to ease the application of the pad onto the patient's skin at a specific site. For example, an area of a patient's skin with an abrupt bend, such as at a joint, can require that the tab be aligned toward one of the lateral ends of the base pad 304 rather than along the center line.

A nurse or other medical practitioner grips a tab 325 and peels the backing 323 off one half of the bottom adhesive layer 322. The tab overcomes any requirement that the nurse pick at a corner edge or other segment of the backing in order to separate the backing from the adhesive layer. The nurse then places the bottom layer 322 against the patient's skin to adhere the base pad 304 to the patient. Light pressure over the upper layer 318 assures good adhesion between the base pad 304 and the patient's skin. The base pad 304, due to its flexibility, conforms to the contours of the topical surface to which the base pad 304 adheres. The nurse then repeats this procedure for the other half of the pad 304.

Alternatively, the nurse may completely remove the backing 323 from the pad 304 before attaching the pad 304 to the patient's skin.

The base pad 304 desirably comprises a notch 324 positioned distal of the location of the retainer 302 on the pad 304 and adjacent to the point of insertion of the needle or other indwelling medical article. The notch 324 is sized to permit visual inspection of the insertion site.

The base pad 304 desirably may comprise indicia 326 in the form of an arrow which indicates the proper orientation of the base pad 304 in reference to insertion site. Although FIGS. 15 and 16 illustrate the indicia in the form of an arrow, it is contemplated that other forms of indicia could be used as well, for example but without limitation, words or other graphics. The indicia 326 should point in the proximal direction, towards the needle, or otherwise indicate the proper location of the pad 304 in reference to the needle or other proximal attachment to the adaptor 12.

In an exemplary embodiment, the laminate structure of the base pad 304 is preferably formed by rolling a paper tape, such as a micro-porous rayon tape, available commercially as MICRO-PORE tape from 3M (Item No. 1530), over a medical grade polyvinyl chloride foam tape, such as that available commercially from 3M (Item No. 9777L). The foam tape preferably includes the bottom liner or backing 323. The base pad 304 and the tabs 325 are then stamped out of the laminated sheet of foam and paper. The backing 323 between the tabs and the base pad, however, is desirably not severed such that the tabs 325 remain attached to the backing covering the adhesive section 322 of the base pad 304. The backing 323 is then cut into two pieces along the centerline of the pad 304 and between the tabs 325.

Tube Clip

FIGS. 15 and 16 also illustrate a tube clip 328. The clip 328 secures the medical line 14 to form a safety loop, as known in the art.

The tube clip 328 has a plate-like base 330 adhered to or embedded in the base pad 304. The tube clip 328 may be located on the base pad 304 on either side of the retainer 302 to accommodate left hand or right hand mounting. The anchoring system 300 may further include a second tube clip (not shown) located on the other side of the retainer 302 from the first tube clip 328.

The clip 328 defines a channel 332 having a generally circular cross-sectional configuration truncated to form an upper orifice 334. The diameter of the channel 332 is desirably slightly less than that of the medical line 14 so as to ensure a secure interconnection. The channel 332 receives a portion of the medical line 14 through the orifice 334 upon application of gentle pressure or by pulling the line 14 across and through the orifice 334 of the tube clip 328, as explained below. The clip 328 surrounds a substantial portion of the medical line 14 with the medical line 14 positioned within the channel 332.

The upper edge of the channel may include tapered ends 336 at the proximal and distal ends of the clip 328. Each tapered end 336 forms a smooth transition between the side edge of the channel 332 and the upper edge, and tapers in lateral width from the side edge toward the center of the tube clip 328. The tapered ends 336 help guide the medical line 14 into the channel 332 when a medical practitioner pulls the medical line 14 across the clip 328. Thus, the practitioner does not have to pinch the line 14 to insert it into the clip 328. Also, the medical practitioner's gloves do not get stuck in the clip 328 when inserting the line 14, as is typically the case where if it is required to pinch the line 14 in order to insert it into the clip 328.

Slide Clamp

Referring to FIG. 16, the anchoring system 300 desirably additionally includes a slide clamp 338 to regulate fluid flow through the medical line 14, as is known in the art. The clamp 338, at one end, includes an aperture 340 which receives the medical line 14, and includes a tab 342 at the opposite end. The clamp 338 has a generally forked shape formed by a pair of prongs 344 that define the aperture 340. The medical line 14 snaps between the prongs 344 and into the aperture 340, which has a diameter slightly larger that the medical line 14.

The prongs 344 converge together in the direction towards the tab 342 to form a tapering slot 346 which opens into the aperture 340. The prongs 344 pinch the medical line 14 closed with the medical line 14 positioned in the slot 346 so as to block fluid flow therethrough. The clamp 338, however, slides over the medical line 14 with the line 14 positioned through the aperture 340.

Finger Platform

With reference to FIGS. 15 and 16, a finger platform 348 extends from the sidewalls 308 of the retainer 302. The finger platform 348 may be located on the base pad 304 on either side of the retainer 302 to accommodate left hand or right hand mounting. The anchoring system 300 may further include a second finger platform (not shown) located on the other side of the retainer 302 from the first finger platform 348. The finger platforms 348 are sized and configured to enable allow a health care provider to press the retainer 302 against the skin of the patient while pulling up on the connector fitting 10 or when disengaging the fitting 10 from the retainer 302.

The components of the anchoring system 300 other than the base pad 304 (i.e., the retainer 302, tube clip 328, slide clamp 338, and finger platform 348), may be constructed in any of a variety of ways well known to one of skill in the art. For instance, each individual component may be integrally molded such as by injection molding or by thermoplasty. The components preferably comprise a durable, flexible material, and more preferably comprise a generally inert, non-toxic material. In a preferred embodiment, the components are molded of plastic, such as, for example, polycarbonate, polyvinylchloride, polypropylene, polyurethane, tetrafluoroethylene (e.g., TEFLON®), polytetrafluoroethylene (a.k.a., PTEF), acetal resin (e.g., DELRIN®), chlorotrifluoroethylene (e.g., KEL-F®), nylon or other polymers.

Securing a Connector Using the Anchoring System

The following discussion of the method of use will be with reference to FIGS. 15 and 16, and initially will be in the context of intravenous catheterization. As the following discussion will illustrate, however, it is understood that the anchoring system 300 can be used in other catheterization procedures as well.

A nurse or other medical practitioner typically begins the catheterization process by positioning the catheter at a desired location above a vein. The medical practitioner introduces a needle or other stylus through a cannula portion of the adaptor 12 and into the skin of the patient at a desired angle of incidence. For intravenous use, the needle commonly has an incident angle of approximately 7°. The distal end of the needle is advantageously pre-connected to a female luer-type adaptor 12.

The nurse attaches the proximal portion 30 of the connector fitting 10 into the adaptor 12 as described above.

The nurse removes the paper backing 323 which initially covers the adhesive bottom surface 322 of the base pad 304, and attaches the pad 304 to the patient's skin proximate to the indwelling needle. Specifically, the nurse grips the backing tab 325 proximate to the retainer 302. The nurse then pulls on the tab 325 and peels the backing off one half of the bottom adhesive layer 322. The nurse positions the slot 324 of the pad 304 around the adaptor 12 with the instructing indicia 326 (e.g., indicating arrow) pointing in the direction of the needle. The nurse then places the bottom layer 322 against the patient's skin to adhere the base pad 304 to the patient. Light pressure over the upper layer 318 assures good adhesion between the base pad 304 and the patient's skin. The base pad 304, due to its flexibility, conforms to the contours of the topical surface to which the base pad 304 adheres. The nurse then repeats this procedure for the other half of the pad 304. Alternatively, the nurse may completely remove the backing 323 from the pad 304 before attaching the pad 304 to the patient's skin.

The nurse orients the radial member 34 of the connector fitting 10 above the series of retainer slots 312. The nurse then snaps the fitting 10 into the retainer 302. In doing so, the fitting 10 is pressed between the longitudinal walls 308 of the retainer 302. As the nurse presses the fitting 10 into the retainer 302, the chamfered edges 316 around the slots 312 of the longitudinal wall 308 guide the radial member 34 into one of the slots 312.

As mentioned above, the upper opening 310 of the channel 306 has a smaller width measured in the lateral direction than the diameter of the elongated body 20 of the fitting 10. The lateral walls 308 thus deflect outwardly in a lateral direction. Once the elongated body 20 of the fitting 10 rests within the central channel 306 of the retainer 302, the lateral walls 308 spring back to snap the fitting 10 in place. The walls 308 of the retainer 302 thus prevent unintentional transverse and lateral movement of the fitting 10 relative to the patient.

The design of the retainer 302 provides for a variety of positions in which the fitting 10 may be secured within the retainer 302; in this way, the usage of the retainer 302 is not technique or position sensitive. In other words, a nurse or other medical practitioner can simply press the fitting 10 into the retainer 302, irrespective of the relative positions of the fitting 10 and any particular slot 312. The radial member 34 will be guided into one of the series of slots 312 by the chamfered edges 316 as long as the member 34 is positioned somewhere above the slots 312.

As FIG. 16 illustrates, the nurse may also form a safety loop in the medical line 14, as is known in the art, and secure the safety loop to the patient by inserting a portion of the line 14 into the tube clip 328. The safety loop absorbs any tension applied to the medical line 14 in order to prevent the connector fitting 10 and/or the adaptor 12 from being pulled.

Those of skill in the art will recognize that the above technique for securing the connector system to the anchoring system 300 may be applied equally well to connector systems which make use of the spin nut 50 and radial member 34 disposed upon the adaptor 12, such as the embodiment shown in FIG. 14. In these cases, the adaptor 12 will be secured directly to the retainer 302 of the anchoring system 300. However, the radial member 34 will be secured within one of the slots 312 of the retainer 302 in the same manner as is described above with respect to FIGS. 15 and 16.

Furthermore, those of skill in the art will appreciate that the techniques described above regarding releasing the connector fitting 10 from the adaptor 12 may be combined with the technique for securing the connector system to the anchoring system 300.

The various embodiments of the connector fitting described above in accordance with the present invention thus provide a means to connect a connector fitting to an adaptor and easily release the medical line from the adaptor using the spin nut. The spin nut is pressed back against the radial member and can be used to transfer force from the fingers of the medical practitioner to the connector fitting in order to separate it from the adaptor.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the shape of the receptacle and radial member may be taken from one of the alternate embodiments shown in FIGS. 8A-12B and applied to a connector system in which the spin nut is on the adaptor, as is shown in FIG. 14. In addition to the variations described herein, other known equivalents for each feature can be mixed and matched by one of ordinary skill in this art to construct releasable connector systems in accordance with principles of the present invention.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A connector fitting in combination with a retainer for releasably securing a medical article to an adaptor with a tubular portion, the connector fitting comprising:

an elongated body having a longitudinal axis, at least a portion of which is adapted to insert into the tubular portion of the adaptor, and at least one radially extending member disposed upon the elongated body, the at least one radially extending member having at least one contact surface; and a spin nut comprising a generally tubular body slidably and rotatably disposed upon the elongated body, a screw thread disposed upon an inner surface of the spin nut, and a receptacle disposed distally upon the spin nut having an internal cross section, the receptacle having at least one contact surface disposed proximally of the distal end of the spin nut, the at least one contact surface configured and arranged to interact with the at least one contact surface of the radially extending member when the receptacle receives at least a portion of the radially extending member so as to transfer both axial and rotational forces between the spin nut and the connector fitting without deforming the spin nut in a direction towards the longitudinal axis, wherein the connector fitting is disposed upon a proximal end of the medical article; and the retainer comprising a channel that extends through the retainer along a longitudinal axis, and at least one slot which receives the at least one radial member of the connector fitting.

2. A connector fitting as in claim 1, wherein the medical article is a medical line.

3. A connector fitting for releasably securing a medical article to an adaptor in combination with a retainer, the connector fitting comprising:

an elongated body with at least one radially extending member disposed upon the elongated body; and a spin nut comprising a generally tubular body slidably and rotatably disposed upon the elongated body, a screw thread disposed upon an inner surface of the spin nut, and a receptacle disposed distally upon the spin nut having an internal cross section which varies radially about its circumference, at least a portion of the radially extending member being adapted to be inserted into the receptacle of the spin nut so as to align with the portion of the receptacle having the varying cross section, said portion extending entirely around an axis of the elongated body; and the retainer comprising a channel that extends through the retainer along a longitudinal axis, and at least one slot which receives the at least one radial member of the connector fitting.

4. A connector fitting as in claim 3, wherein the medical article is a medical line.

5. A connector fitting for releasably securing a medical article to an adaptor with a tubular portion, the connector fitting comprising:

an elongated body, at least a portion of which is adapted to insert into the tubular portion of the adaptor, and at least one radially extending member disposed upon the elongated body, the at least one radially extending member having at least one contact surface;

a spin nut comprising a generally tubular body slidably and rotatably disposed upon the elongated body, a screw thread disposed upon an inner surface of the spin nut, and a receptacle disposed distally upon the spin nut having an internal cross section, the receptacle having at least one contact surface disposed proximally of a distal end of the spin nut, the at least one contact surface configured and arranged to interact with the at least one contact surface of the radially extending member when the receptacle receives at least a portion of the radially extending member so as to transfer both axial and rotational forces between the spin nut and the connector fitting without deforming the spin nut, wherein the connector fitting is disposed upon a proximal end of the medical article; and wherein the connector fitting includes a second radially extending member which is configured to cooperate with a slot of an anchoring system.

6. A connector fitting as in claim 5, wherein the medical article is a medical line.

7. A connector fitting for releasably securing a medical article to an adaptor with a tubular portion, the connector fitting comprising:

an elongated body, at least a portion of which is adapted to insert into the tubular portion of the adaptor, and at least one radially extending member disposed upon the elongated body, the at least one radially extending member having at least one contact surface; and a spin nut comprising a generally tubular body slidably and rotatably disposed upon the elongated body, a screw thread disposed upon an inner surface of the spin nut, and a receptacle disposed distally upon the spin nut having an internal cross section, the receptacle having at least one contact surface disposed proximally of a distal end of the spin nut, the at least one contact surface configured and arranged to interact with the at least one contact surface of the radially extending member when the receptacle receives at least a portion of the radially extending member so as to transfer both axial and rotational forces between the spin nut and the connector fitting without deforming the generally tubular body of the spin nut, wherein the connector fitting is disposed upon a proximal end of the medical article, and wherein the internal cross section of the receptacle of the spin nut has a generally hexagonal shape.

8. A connector fitting as in claim 7, wherein the medical article is a medical line.

9. A connector fitting for releasably securing a medical article to an adaptor with a tubular portion, the connector fitting comprising:

an elongated body, at least a portion of which is adapted to insert into the tubular portion of the adaptor, and at least one radially extending member disposed upon the elongated body, the at least one radially extending member having at least one contact surface; and a spin nut comprising a generally tubular body slidably and rotatably disposed upon the elongated body, a screw thread disposed upon an inner surface of the spin nut, and a receptacle disposed distally upon the spin nut having an internal cross section, the receptacle having at least one contact surface disposed proximally of a distal end of the spin nut, the at least one contact surface configured and arranged to interact with the at least one contact surface of the radially extending member when the receptacle receives at least a portion of the radially extending member so as to transfer both axial and rotational forces between the spin nut and the connector fitting without deforming the generally tubular body of the spin nut, wherein the connector fitting is disposed upon a proximal end of the medical article, and wherein the internal cross section of the receptacle of the spin nut has a star shape.

10. A connector fitting as in claim 9, wherein the medical article is a medical line.

11. A connector fitting for releasably securing a medical article to an adaptor with a female portion, the connector fitting comprising:

an elongated body extending along an axis and having a first section and a second section with a lumen through both sections, a proximal end portion of the second section having a tapering outer shape configured for insertion into the female portion of the adaptor, and at least one contact member disposed on the first section of the elongated body, the contact member extending outwardly relative to an outer surface of the elongated body and extending generally in a longitudinal direction, the contact member having at least one contact surface; and a spin nut comprising a generally tubular body slidably and rotatably disposed on the first section of the elongated body, a screw thread formed on an inner surface of the spin nut, the inner surface being disposed apart from the elongated body such that the screw thread does not engage with the elongated body, and a receptacle disposed distally upon the spin nut, the receptacle having at least one contact surface being disposed within the receptacle, the contact member extending inwardly towards the outer surface of the elongated body and extending generally in the longitudinal direction, the at least one contact surface configured and arranged to interact with the at least one contact surface of the contact member when the receptacle receives at least a portion of the contact member so as to transfer both axial and rotational forces between the spin nut and the connector fitting while limiting distal longitudinal movement of the spin nut relative to the elongated body, wherein the spin nut and the elongated body include cooperative structures that limit proximal longitudinal movement of the spin nut relative to the elongated body.

12. A connector fitting as in claim 11, wherein the cooperative structures include a retaining ridge disposed on the elongated body.

13. A connector fitting as in claim 11 in combination with a retainer comprising a channel that extends through the retainer along a longitudinal axis, and at least one slot which receives the at least one contact member of the connector fitting.

14. A connector fitting as in claim 11 wherein the receptacle has an internal cross section with a generally hexagonal shape.

15. A connector fitting as in claim 11, wherein the receptacle has an internal cross section with a star shape.

16. A connector fitting as in claim 11, wherein the medical article is a medical line.

17. A connector fitting as in claim 11, wherein the contact member on the elongated body extends perpendicular to the axis of the elongated body.

18. A connector fitting as in claim 11, wherein the at least one contact surface of the elongated body and the at least one contact surface of the spin nut lie generally parallel to the axis of the elongated body.

19. A connector fitting for releasably securing a medical article to an adaptor having a female portion, the connector fitting comprising:
    an elongated body having a tapering proximal end and at least one radially extending member disposed upon the elongated body, the tapering proximal end being configured for insertion into the female portion of the adapter, the at least one radially extending member having an external cross section with at least one contact surface disposed on the periphery of the radially extending member and being generally aligned with a longitudinal axis of the elongated body; and
    a spin nut comprising a generally tubular body slidably and rotatably disposed on the elongated body, a screw thread being formed on an inner surface of the spin nut and extending about the elongated body but not connecting with the elongated body, and a receptacle disposed distally upon the spin nut having an internal cross section which corresponds in shape to the external cross section of the at least one radially extending member, at least a portion of the radially extending member being adapted to be inserted into the receptacle of the spin nut, said portion extending entirely around the axis of the elongated body,
    wherein the spin nut and the elongated body include cooperative structures that limit proximal longitudinal movement of the spin nut relative to the elongated body.

20. A connector fitting as in claim 19, wherein the cooperative structures include a retaining ridge disposed on the elongated body.

21. A connector fitting as in claim 19 in combination with a retainer comprising a channel that extends through the retainer along a longitudinal axis, and at least one slot which receives the at least one radial member of the connector fitting.

22. A connector fitting as in claim 19, wherein the medical article is a medical line.

23. A connector fitting for releasably securing a medical article to an adaptor having a female portion, the connector fitting comprising:
    an elongated body having a tapering end portion configured to be inserted into the female portion of the adaptor, and at least one radially extending member disposed upon the elongated body, the at least one radially extending member having multiple contact surfaces; and
    a spin nut comprising a generally tubular body slidably and rotatably disposed upon the elongated body and being configured to secure to an adaptor independent of the radially extending member, and having multiple contact surfaces disposed upon the spin nut, the multiple contact surfaces of the spin nut corresponding in shape to the multiple contact surfaces of the radially extending member so as to transfer both axial and rotational forces between the spin nut and the connector fitting while limiting distal longitudinal movement of the spin nut relative to the elongated body, wherein the spin nut further comprises a receptacle disposed distally upon the spin nut and wherein the at least one contact surface of the spin nut is disposed within the receptacle of the spin nut,
    wherein the spin nut and the elongated body include cooperative structures that limit proximal longitudinal movement of the spin nut relative to the elongated body.

24. A connector fitting as in claim 23, wherein the cooperative structures include a retaining ridge disposed on the elongated body.

25. A connector fitting as in claim 23, wherein the medical article is a medical line.

26. A connector fitting for releasably securing a medical article to an adaptor having a female portion, the connector fitting comprising:
    an elongated body, at least an end portion having a tapering shape configured for insertion into the female portion of the adaptor, the elongated body having at least one radially extending member disposed upon the elongated body, the radially extending member having at least one contact surface disposed on the periphery of the radially extending member; and
    a spin nut disposed upon the elongated body and having a first cavity portion and a second cavity portion, the first cavity portion and the second cavity portion being disposed on opposite ends of the spin nut, the first cavity portion having a screw thread formed on an inner surface and being configured to secure to the adapter and not to the elongated body, the second cavity portion having at least one contact surface disposed upon an inner surface, the at least one contact surface of the spin nut configured and arranged to interact with the at least one contact surface of the radially extending member so as to transfer both axial and rotational forces between the spin nut and the connector fitting without deforming the second cavity portion and while limiting distal longitudinal movement of the spin nut relative to the elongated body.

27. A connector fitting as in claim 26, wherein the spin nut and the elongated body include cooperative structures that limit proximal longitudinal movement of the spin nut relative to the elongated body.

28. A connector fitting as in claim 26, wherein the cooperative structures include a retaining ridge disposed on the elongated body.

29. A connector fitting as in claim 26, wherein the engagement between the spin nut and the radially extending member when the spin nut is in a distal position provides transfer of distally directed force from the spin nut to the connector fitting and provides transfer of rotational torque from the spin nut to the connector fitting.

30. A connector fitting as in claim 26, wherein a greatest radius of the radially extending member is greater than a least radius of the receptacle.

31. A connector fitting as in claim 26, wherein the connector fitting includes a second radially extending member which is configured to cooperate with a slot of an anchoring system.

32. A connector fitting as in claim 26, wherein the medical article is a medical line.

\* \* \* \* \*